US011911255B1

(12) United States Patent
Busso

(10) Patent No.: US 11,911,255 B1
(45) Date of Patent: Feb. 27, 2024

(54) SYSTEMS AND METHODS FOR SUPERFICIAL FACIAL FAT PAD REPOSITIONING

(71) Applicant: Mariano Busso, Miami, FL (US)

(72) Inventor: Mariano Busso, Miami, FL (US)

( * ) Notice: Subject to any disclaimer, the term of this patent is extended or adjusted under 35 U.S.C. 154(b) by 187 days.

(21) Appl. No.: 17/584,040

(22) Filed: Jan. 25, 2022

Related U.S. Application Data

(60) Provisional application No. 63/220,787, filed on Jul. 12, 2021.

(51) Int. Cl.
*A61B 17/06* (2006.01)
*A61B 17/34* (2006.01)
*A61F 2/00* (2006.01)

(52) U.S. Cl.
CPC ...... *A61F 2/0059* (2013.01); *A61B 17/06166* (2013.01); *A61B 17/3468* (2013.01)

(58) Field of Classification Search
CPC ............ A61B 17/3468; A61B 17/0401; A61B 17/282; A61B 17/06166; A61B 17/06; A61B 17/06109; A61B 17/0482; A61B 17/0469; A61B 17/06004; A61B 2017/00792; A61B 2017/06052; A61B 2017/0469; A61B 2017/06171; A61B 2017/06176; A61F 2/0059; A61F 2/0811; A61F 2220/0075
See application file for complete search history.

(56) References Cited

U.S. PATENT DOCUMENTS

| 7,494,488 | B2 | 2/2009 | Weber |
| 7,601,164 | B2 | 10/2009 | Wu |
| 7,850,700 | B2 | 12/2010 | Sakura |
| 8,721,666 | B2 | 5/2014 | Schroeder et al. |
| 9,681,867 | B2 | 6/2017 | Mercelis et al. |
| 11,045,299 | B2 | 6/2021 | Kim |
| 2002/0198544 | A1* | 12/2002 | Uflacker ............... A61F 2/0059 606/144 |
| 2007/0173887 | A1 | 7/2007 | Sasaki |

OTHER PUBLICATIONS

Tonks S., Understanding thread lifting: On line aestheticsjournal.com. https://aestheticsjournal.com/feature/understanding-thread-lifting., Oct. 1, 2015.
Park TH, Seo SW, Whang KW., Facial rejuvenation with fine-barbed threads: the simple Miz lift. Aesthet Plast Surg. 2014;38:69-74, Jan. 1, 2014.
Park TH, Whang KW, Facial rejuvenation using a combination of lateral SMASectomy and thread-lifts, Jan. 1, 2015.

(Continued)

*Primary Examiner* — Majid Jamialahmadi
(74) *Attorney, Agent, or Firm* — Malloy & Malloy, PL

(57) ABSTRACT

A method of superficial fat pad repositioning is disclosed in which three lifting vectors are established which synergistically cooperate to produce an enhanced lifting effect. A first lifting vector is substantially vertical and originates in the superficial orbital fat pad. A second lifting vector is oblique and originates below the nasolabial fold. A third lifting vector is also oblique and originates below the mandible. In a preferred embodiment, monofilament threads are utilized to establish each lifting vector.

10 Claims, 4 Drawing Sheets

(56) References Cited

OTHER PUBLICATIONS

Paul MD, Barbed sutures in aesthetic plastic surgery: evolution of thought and process. Aesthet Surg J. 2013;33(3 Suppl):17S-31S, Jan. 1, 2013.
Sasaki GH, Komorwska-Timek ED, Bennett DC, Gabriel A., An objective comparison of holding, slippage, and pull-out tensions for eight suspension sutures in the malar fat pads of fresh-frozen human cadavers. Aesthet Surg J. 2008;28:387-396, Jan. 1, 2008.
Savoia A, Accardo C, Vannini F, et al., Outcomes in thread lift for facial rejuvenation: a study performed with happy lift revitalizing, Jan. 1, 2014.
Suh DH, Jang HW, Lee SJ, et al., Outcomes of polydioxanone knotless thread lifting for facial rejuvenation. Dermatol Surg. 2015; 41:720-725, Jan. 1, 2015.
Sulamanidze MA, Fournier PF, Paikidze TG, Sulamanidze GM, Removal of facial soft tissue ptosis with special threads. Dermatol Surg. 2002;28:367-371, Jan. 1, 2002.
Wu WT, Barbed sutures in facial rejuvenation. Aesthet Surg J. 2004;24:582-587, Jan. 1, 2004.
Abraham RF, Defatta RJ, Williams EF 3rd., Thread-lift for facial rejuvenation: assessment of long-term results. Arch Facial Plast Surg. 2009;11(3):178-183, Jan. 1, 2009.
Braun M, Frank K, Freytag DL, et al., The influence of the insertion angle on middle and lower face tissue-mechanics when treating the nasolabial folds with facial suspension threads—an experimental split-face cadaveric study., Jan. 1, 2020.
Mariano Busso MD, A New Approach to Thread Facelifting, Oct. 1, 2021.
De Benito J, Pizzamiglio R, Theodorou D, Arvas L., Facial rejuvenation and improvement of malar projection using sutures with absorbable cones: surgical technique and case series. Aesthetic Plastic Surg. 2011; 35:248-253, Jan. 1, 2011.
De Carolis V, Gonzalez M., Neck rejuvenation with mastoid-spanning barbed tensor threads (MST operation). Aesthet Plast Surg. 2014;491-500, Jan. 1, 2014.
Douse-Dean T, Jacob CL., Fast and easy treatment for reduction of Tyndall effect secondary to cosmetic use of hyaluronic acid, Jan. 1, 2008.
Eremia S, Willoughby MA, Novel face-lift suspension suture and inserting instrument: use of large anchors knotted into a suture with attached needle and inserting device allowing for single entry point placement of suspension suture., Jan. 1, 2006.
Gulbitti HA, Colebunders B, Pirayesh A, et al., Thread-lift sutures: still in the lift? a systematic review of the literature. Plast Reconstr Surg. 2018;141:341e-347e., Jan. 1, 2018.
Huggins RJ, Freeman ME, Kerr JB, Mendelson BC, Histologic and ultrastructural evaluation of sutures used for surgical fixation of the SMAS., Jan. 1, 2007.
Kalra R., Use of barbed threads in facial rejuvenation. Indian J Plast Surg. 41(suppl):S93-S100, Jan. 1, 2008.

\* cited by examiner

SYSTEMS AND METHODS FOR SUPERFICIAL FACIAL FAT PAD REPOSITIONING

The present application is based on, and a claim of priority is made under 35 U.S.C. Section 119(e) to a provisional patent application that is currently pending in the U.S. Patent and Trademark Office, namely, that having Ser. No. 63/220,787 and a filing date of Jul. 12, 2021, and which is incorporated herein by reference.

BACKGROUND OF THE INVENTION

Field of the Invention

The invention pertains to methodologies for the use of contour or monofilament threads during aesthetic procedures.

Description of the Related Art

Traditional "face lift" surgical procedures often involve highly invasive rearrangement of facial tissues, which leads to scarring, complications, and a range of negative effects. More recently, so-called "contour threads" have been developed to address the shortcomings of the surgical procedure. The contour threads are typically used to lift facial tissues suffering from ptosis and encourage collagen production in order to "bulk" or "volumize" sunken areas. Instead of highly invasive surgery involving the rearrangement of facial tissue, the threads are simply injected into or near the affected areas. The threads are typically made from a single filament of synthetic material—a so called "monofilament." Monofilament threads for use in contour thread procedures are typically made from polydioxanone ("PDO") but can also be made from Poly-L-Lactic Acid ("PLLA") or Polycaprolactone ("PCL") depending upon the desired purpose or lifespan of the threads.

One popular use for monofilament threads, beyond volumizing or bulking, is for face lift-like procedures resulting from the development of "tissue-engaging" threads which can be anchored at one end and used to lift tissue at another end. In this regard, some success has been had in using monofilament threads to address sagging facial features and lines caused by ptosis, however better, more efficient results are still desired. In particular, and, in comparison to a traditional surgical "face lift" procedure, the results can be subtle. Even though tissue-engaging threads can somewhat lift the patient's facial tissue, the threads tend to be less effective when addressing heavy or frequently used tissues, such as mouth, cheeks, and jowls. Notably, contour threads are not anchored to the patient's skull or deep within tissue; the threads are anchored in the same superficial fat layers in which the rest of the thread is injected. This is desirable for a non-invasive procedure. Overloading the threads, however, can lead to failure of the tissue engaging portions of the threads. Some efforts have been made to anchor threads and similar lifting implants deeper within the facial tissue, and even to the patient's bone. However, these methods are highly invasive and difficult to reverse. Therefore, there is a need in the art for techniques which utilize contour threads in a more efficient manner, without causing the procedure to become more invasive.

SUMMARY OF THE INVENTION

The present invention, therefore, addresses these and other needs in the art by combining multiple lifting vectors to establish synergistic results previously unavailable with contour threads injected into superficial fat layers. More specifically, the present invention addresses many of the typical indications for a "face lift" type aesthetic procedure, such as sunken fat pads around the eyes, enlarged nasolabial folds, as well as ptosis of the jowl fat deposits. Targeting these three areas in accordance with the embodiments set forth herein will result in superior and more efficient lifting of the tissue than is otherwise achievable.

A first lifting vector in accordance with the present invention can comprise a substantially vertical lifting vector originating in the superficial orbital fat pad. In a preferred embodiment the region is volumized or "bulked" in order to tighten the skin and create a substantially vertical lifting force in the regions below the orbital fat pad, including the nasolabial fat pad and the jowl fat pad. In a most preferred embodiment, collagen production in the region is encouraged via the injection of one or more monofilament threads which are non-tissue engaging, but other methods may be utilized. It will be appreciated that results from the foregoing may not be appreciated immediately as it typically takes one to two months for collagen to finish forming in the region.

With respect to the first vector, the inventor has achieved satisfactory results with the following procedure. The superior face of the zygomatic bone is selected as an anchoring point for four, 50 mm mesh threads, which are inserted with an 18-guage needle with the bevel up. The threads are placed between the zygomatic bone and the fat pads in order to elevate the fat pad.

A second lifting vector in accordance with the present invention is substantially oblique and originates below the nasolabial fold near the upper lip. The vector points above the patient's ear in a direction toward the zygomatic retaining ligament. One or more tissue engaging threads may be injected along this vector in order to lift the tissue in the region, thereby decreasing the magnitude of the nasolabial fold and lifting the nasolabial orbital fat pad. In a preferred embodiment, the tissue engaging threads are inserted with a hollow cannula and the cannula is rotated approximately 45 degrees each time a superficial fat septum is perforated. Such a technique is beneficial when the cogs are disposed in the same plane along the thread, instead of a helical or other distribution. Once inserted, the thread is anchored with anchoring cogs and the tissue is lifted onto lifting cogs to achieve the desired lift. Additional tissue engaging threads may inserted near and/or parallel to the second lifting vector if desired.

With respect to the second lifting vector, the inventor has achieved satisfactory results with the following procedure. Using an 18-guage needle, create an entry point with the bevel up and the needle approximately parallel to the skin. Tilt the patient's head slightly to accentuate the effects of gravity (the patient is ideally seated in an upright position). Pinch or fold the skin to create a "tunnel" of subcutaneous fat along the vector. Begin advancing the cannula through the "tunnel" until resistance from a fat septum is felt. Upon perforating a fat septum, rotate the cannula approximately 45 degrees and continue to advance the cannula, rotating each time a fat septum is perforated. Upon reaching the distal end of the vector, typically around McGregor's patch, the index finger should be used to stretch the skin on the anchoring area to prevent skin folds. Then, while stretching the skin on the anchoring area with the index finger, use the thumb to reposition the superficial fat pad to the desired location, thus maintaining the distance between the first lifting cog and the last anchoring cog. If the thread were to "bunch" in this area, a skin fold could be produced. Before releasing the thread from the cannula, distribute the tissue along the cannula so that the fat pad falls where the lifting cogs are located.

A third lifting vector in accordance with the present invention is also substantially oblique and originates below the mandible under the jowl fat pat. The vector points above the patient's ear in the direction of the masseteric retaining ligament and in certain embodiments may be more specifically directed between the masseteric and zygomatic retaining ligaments. One or more tissue engaging threads may be injected along this vector in order to lift the tissue along the vector, thereby raising any sagging tissue along the mandible, such as the jowl fat pad. In a preferred embodiment, the tissue engaging threads are inserted with a hollow cannula and the cannula is rotated approximately 45 degrees each time a superficial fat septum is perforated. Once inserted, the thread is anchored with anchoring cogs and the tissue is lifted onto lifting cogs to achieve the desired lift. Additional tissue engaging threads may be inserted near and/or parallel to the third lifting vector if desired.

With respect to the third lifting vector, the inventor has achieved satisfactory results with the following procedure. Using an 18-guage needle, create an entry point with the bevel up and the needle approximately parallel to the skin. Tilt the patient's head slightly to accentuate the effects of gravity (the patient is ideally seated in an upright position). Pinch or fold the skin to create a "tunnel" of subcutaneous fat along the vector. Begin advancing the cannula through the "tunnel" until resistance from a fat septum is felt. Upon perforating a fat septum, rotate the cannula approximately degrees and continue to advance the cannula, rotating each time a fat septum is perforated. Upon reaching the distal end of the vector, typically around the less mobile masticatory region between the zygomatic and masseteric ligaments, the index finger should be used to stretch the skin on the anchoring area to prevent skin folds. At this point, the cannula hub should have lifted the entry point under the mandible to the base of the mandible. Then, while stretching the skin in the anchoring area with the index finger, use the thumb to reposition the superficial fat pad to the desired location, thus maintaining the distance between the first lifting cog and the last anchoring cog. If the thread were to "bunch" in this area, a skin fold could be produced. Before releasing the thread from the cannula, distribute the tissue along the cannula so that the fat pad falls where the lifting cogs are located.

In yet further embodiments a plurality of lifting threads may be inserted along substantially the same vector, or parallel to the vector. These threads may then be tied in a knot at the lifting end, thereby providing additional structure to help lift the tissue.

When all three lifting vectors have been established, an overall lifting effect that is far superior to what has previously been achievable with contour threads alone is established. As may be understood, the threads in each vector need only shoulder a portion of the full load. Thus, the typical problems that arise when the threads are pushed to maximum capacity, such as damage to the cogs or threads escaping the tissue, can also be avoided.

Now that the details of the particular lifting vectors have been disclosed, it is helpful to address a number of principals which inform the procedure and help achieve optimal results. Initially, the entry point for each thread should be proximal to the area of greatest mobility (e.g., the particular fat pad that is to be lifted). This approach offers greater control over placement of the threads as compared to the typical entry at the distal anchor point. A desired entry point is approximately two centimeters from the fat pad to be lifted, in order to ensure that the first lifting cog coincides with the medial boundary of the fat pad. It is also more desirable to select one oblique vector per fat pad and to avoid vectors in different directions.

Another principal is to distribute the target tissue to be lifted along the cannula when placing the lifting cogs. This assures that the area to be lifted coincides with the distribution of lifting cogs on the threads. In order for this to occur, it is imperative for the person conducting the procedure to be familiar with the geometry of the thread. One way to help achieve this result is to position the fat pad where desired for a final lift before inserting the cannula.

Another general principal to be observed is to introduce the cannula with the bevel up and advance that cannula such that it perforates as many vertical fat septa as possible. In this regard, the lifting and anchoring cogs can interface with the fat septa to provide better tissue holding and repositioning and reduce the likelihood of slippage. A final principal to consider is to avoid manipulation of the tissue after the thread is released in order to maintain the distance between the first lifting cog and final anchoring cog. If this distance is shortened, such as if the thread were to "bunch," wrinkles and folds in the skin can be introduced.

The present invention is also believed to provide a mechanobiological adaptation or stimulus, which lengthens the effects beyond the life span of the threads. In particular, reorientation of the skin by using the three vectors disclosed above will naturally slacken some ligaments and stretch others. This will lead to redistribution and/or formation of collagen in new areas, thus leading to a more permanent change in the patient's facial tissue.

The tissue engaging threads disclosed herein may be made of any of a variety of known monofilaments and, in a preferred embodiment, are made from PDO. Additionally, the lifting and anchoring cogs can be formed from a variety of known geometries, such as burs or harpoons, which are suitable for anchoring the threads within tissue as well as supporting lifted tissue.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
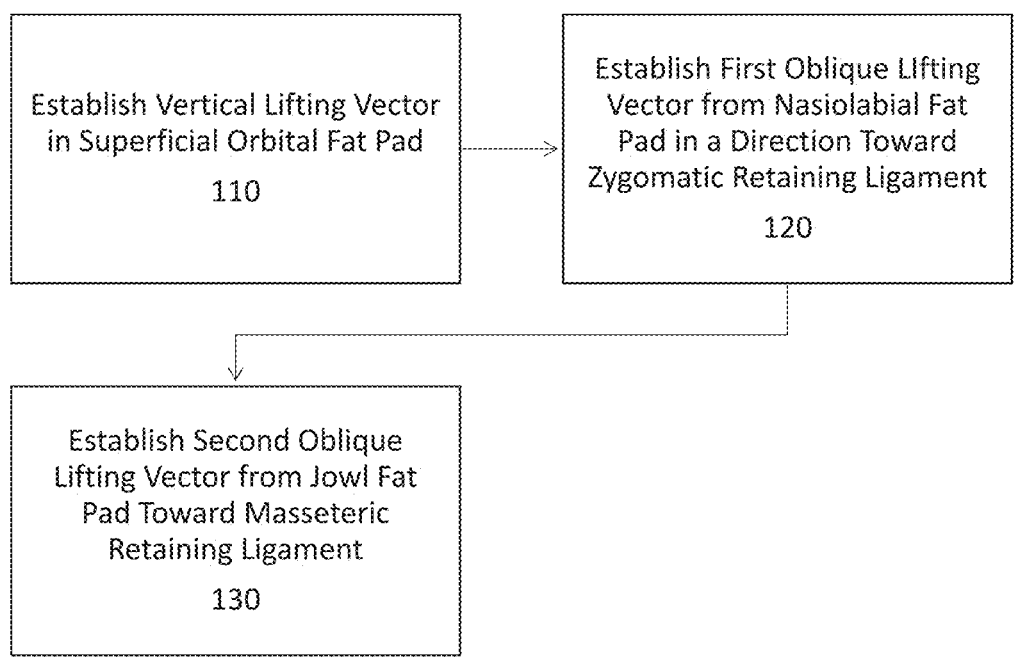
FIG. 1 is a schematic depiction the general steps of a method in accordance with one embodiment of the present invention.

FIG. 1 is a schematic depiction of the general steps of a method 100 according to one embodiment of the present invention. A first step of the method 100 comprises establishing a vertical lifting vector within the superficial orbital fat pad of the patient 110. A variety of known methodologies exist to establish the vertical lifting vector however, as will be disclosed below, one preferred and inventive embodiment can comprise injecting at least one monofilament thread into the superficial orbital fat pad to encourage collagen production in the region. A second step of the method can comprise establishing a first oblique lifting vector from the nasolabial fat pad generally in a direction toward the zygomatic retaining ligament 120. A variety of known methodologies exist to establish the first oblique lifting vector however, as will be disclosed below, one preferred and inventive embodiment can comprise injecting at least one monofilament thread below the nasolabial fold, the at least one monofilament thread having a portion of anchoring cogs and a portion of lifting cogs. The third step of the method can comprise establishing a second oblique lifting vector from the jowl fat pad in a direction generally toward the masseteric retaining ligament 130. In certain embodiments, it may be desirable to direct the second oblique lifting vector more specifically between the masseteric and zygomatic retaining ligaments. A variety of known methodologies exist to establish the second oblique lifting vector however, as will be disclosed below, one preferred and inventive embodiment can comprise injecting at least one monofilament thread below the mandible, the at least one monofilament thread having a portion of anchoring cogs and a portion of lifting cogs.

Figure 2:
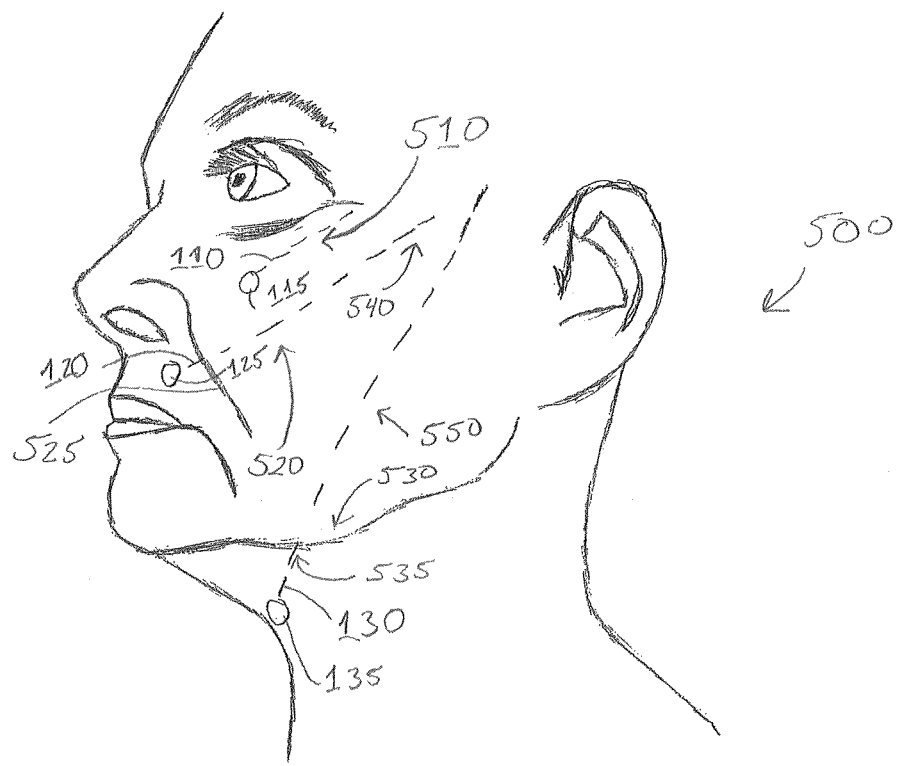
FIG. 2 is a depiction of a patient prior to having an aesthetic procedure done in accordance with the method of the present invention wherein a plurality of injection vectors have been marked on the patient's face.

FIG. 2 is a depiction of a pre-procedure patient 500 showing the various injection vectors marked on the patient's face. As can be seen the patient 500 is showing several indications which can be addressed via the methods of the present invention, including a superficial orbital fat pad 510 having a "sunken" appearance, as well as a pronounced nasolabial fold 525 extending downwardly, and the jowl fat pad 535 is exhibiting ptosis due to gravity and relaxation of the patient's skin and muscles. In accordance with one embodiment of the present invention, several lifting vectors can be established to address each of these indications, and which will result in superior results, especially with regard to the jowl fat pad, then heretofore have been established using contour threads alone. The lifting vectors, in at least one embodiment, can be established with several injection vectors as will be described.

The first vertical lifting vector 110 is located in the superficial orbital fat pad 510 of the patient. The first injection vector 115 lies at the lower extreme of the inferior orbital compartment and runs in a direction laterally and upwards across the patient's superficial orbital fat pad toward the lateral orbital compartment. The first oblique lifting vector 120 lies within the nasolabial compartment and may extend into the middle cheek compartment and beyond, as high as the lateral orbital compartment. The second injection vector 125 begins at the patient's cutaneous upper lip just below the nasolabial fold 120. While one of ordinary skill in the art will appreciate that the injections should run along the patient's subcutaneous fat layer, and should not reach the patient's ligaments, it is nevertheless helpful to refer to facial ligaments as guidelines for injection vectors. As such, the second injection vector 125 may extend upwards and laterally substantially toward the zygomatic retention ligament 520 and extend as far along the patient's face as is necessary to securely anchor the thread and achieve the desired outcome. The second oblique lifting vector 130 is below the first oblique lifting vector 120 and extends from below the mandible 535 toward the masseteric retaining ligament 550.

Figure 3:
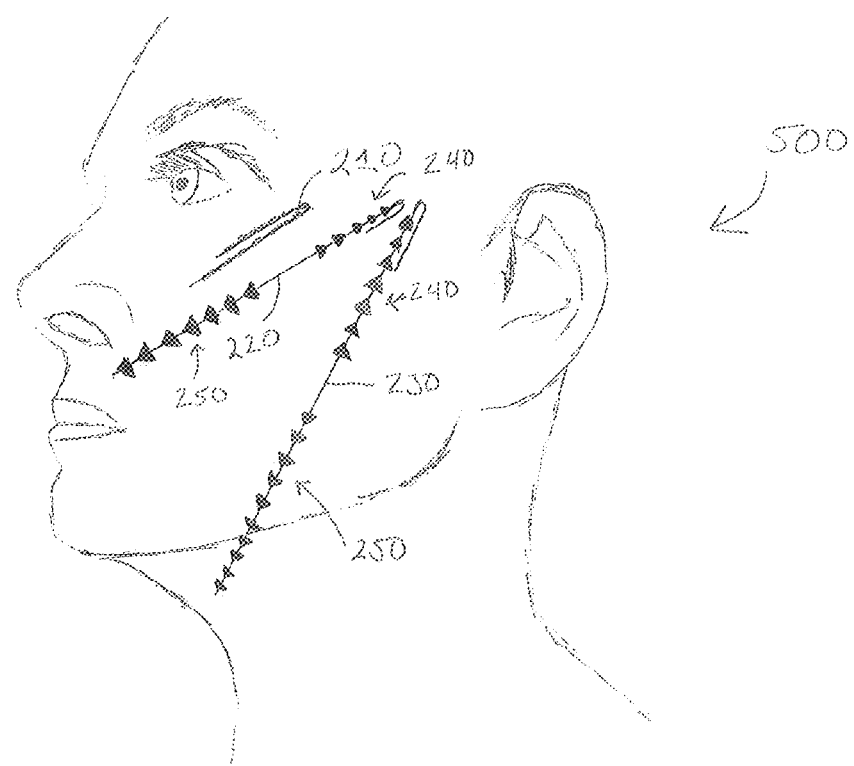
FIG. 3 is a depiction of a patient after having an aesthetic procedure done in accordance with the method of the present invention showing a plurality of monofilament threads injected into the patient's face. The monofilament threads are shown as visible to aid in disclosure despite that they would not normally be visible being injected below the skin.

FIG. 3 depicts a patient 500 post-procedure wherein a plurality of monofilament threads have been inserted under the patient's skin. For purposes of facilitating disclosure, the threads have been depicted as visible even though they would not be visible under the patient's skin after the procedure. In a preferred embodiment, and referencing both FIGS. 2 and 3, a first monofilament thread 210 is injected into the patient's superficial orbital fat pad 510. The first monofilament thread 210 can be any of a variety that are known to "volumize" by encouraging collagen production. This may be accomplished by injecting a plurality of single threads into the area, or by the use of a "mesh" thread or "screw" thread, or, as depicted, a braided thread may be used. Volumizing or bulking the subcutaneous tissue in this region creates a substantially vertical lifting vector throughout the tissue below it, including the nasolabial fat pad as well as the jowl fat pad.

A second monofilament thread 220 may be injected below the first monofilament thread 210 along the second injection vector 125 described above. In a preferred embodiment, the second monofilament thread 220 includes a plurality of anchoring cogs 240 at one end and a plurality of lifting cogs 250 at another end. For purposes of the present disclosure the lifting and anchoring cogs may be any of a variety of known structures, such as barbs or harpoons, which are designed to engage with the tissue and support or lift the tissue. Anchoring cogs 240 are dimensioned and configured to resist "pull-out" of the thread once inserted. Stated otherwise, the anchoring cogs 240 serve to "anchor" the thread within the tissue and resist retrograde motion of the thread outwardly along the injection vector. Lifting cogs 250, on the other hand, are dimensioned and configured oppositely to anchoring cogs 240. Instead of anchoring the thread within the tissue, lifting cogs 250 support the tissue to be lifted in that they are dimensioned and configured to resist sagging of the tissue once the thread is injected. Stated otherwise, the lifting cogs 250 serve to resist prograde motion of the thread inwardly along the injection vector. The third monofilament thread 230 is configured similarly to the second monofilament thread 220 in that it includes both anchoring cogs 240 and lifting cogs 250 on opposite ends of the threads, except that the third monofilament thread 230 can be longer than the second monofilament thread 220.

Figure 4:
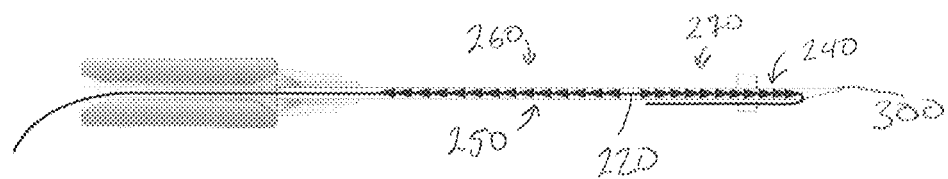
FIG. 4 is a depiction of one monofilament threaded loaded into a cannula to be used in accordance with one embodiment of the present invention.
Figure 5:
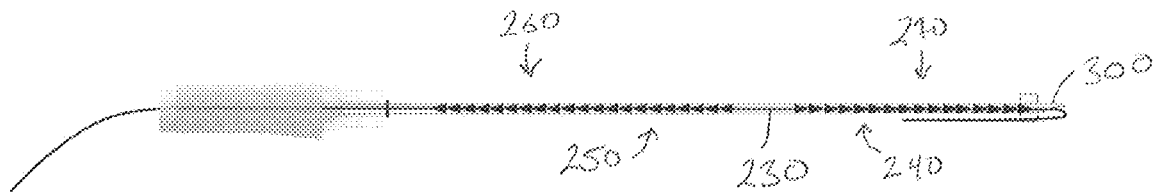
FIG. 5 is a depiction of one monofilament threaded loaded into a cannula to be used in accordance with one embodiment of the present invention.
Figure 6:
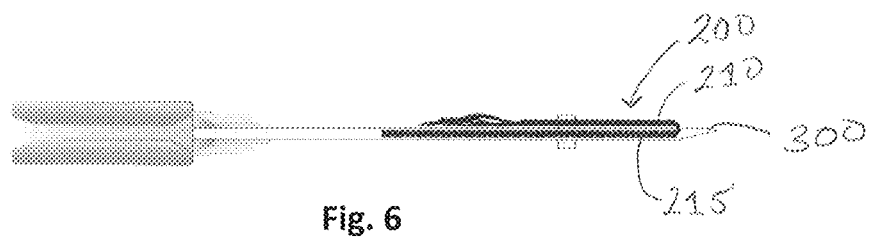
FIG. 6 is a depiction of one monofilament threaded loaded into a cannula to be used in accordance with one embodiment of the present invention.

FIGS. 4-6 depict preferred embodiments for first, second, and third monofilament threads which have been pre-loaded into cannula 300 and ready for injection into a patient. Beginning with FIG. 4, a preferred embodiment of a second monofilament thread 220 is shown. The second monofilament threads may include an approximately 2 cm long section of anchoring cogs 240 and an approximately 3 cm long section of lifting cogs 250 separated by an approximately 0.3 cm interstitial space. The second monofilament thread 220 is loaded into the cannula such that the anchoring cogs 240 are on the distal end 270 of the cannula 300, while the lifting cogs 250 are located on the proximal end 260 of the cannula 300. In a preferred embodiment, a tail of approximately 4.5 cm can be threaded through the hollow proximal end 260 of the cannula 300 which can assist with final placement of the tissue onto the lifting cogs 260 and can be trimmed to length once implanted. Additionally, a lead length of approximately 2 cm can be left protruding from the distal end 270 of the cannula 300 to facilitate injection and placement of the second monofilament thread 220 within the patient.

FIG. 5 is a preferred embodiment of the third monofilament thread 230 disposed within a cannula 300. The third monofilament thread 230 can include a section of anchoring cogs 240 approximately 3.5 cm long, a second of lifting cogs 250 approximately 4.5 cm long, and an interstitial separation of 9.9 cm separating the anchoring cogs 240 from the lifting cogs 250. The third monofilament thread 230 is loaded into the cannula 300 such that the anchoring cogs 240 are disposed on the distal end 270 of the cannula 300, while the lifting cogs 250 are disposed on the proximal end of the cannula 300. Additionally, a tail end of at least 6.6 cm and a lead length of 2.5 cm provide sufficient length for ease of implantation and affixing the tissue to the lifting cogs 250.

FIG. 6 depicts a first monofilament thread 210 which is preferably a braided thread 215 and at least 7.5 cm in length. The first monofilament thread 210 is loaded into the cannula 300 such that approximately 3.5 cm protrudes externally of the cannula 300, leaving approximately 4 cm inside the cannula 300.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method for facial, superficial fat pad repositioning in a patient, the method comprising:
    inserting at least one first monofilament thread into the patient's superficial orbital fat pad;
    inserting at least one second monofilament thread into the patient's nasolabial fat pad, entering approximately at the nasolabial fold and advancing the at least one second monofilament thread at least as far as the zygomatic retaining ligament;
    inserting at least one third monofilament thread into the patient's jowl fat pad, entering below the mandible and advancing the at least one third monofilament thread at least as far as the masseteric retaining ligament;
    wherein each of the at least one first, second, and third monofilament threads are inserted with a cannula; and
    rotating the cannula approximately 45 degrees each time a superficial fat septum is perforated as the cannula is advanced when inserting at least one of the at least one second and third monofilament threads.

2. The method as recited in claim 1 wherein the at least one first monofilament thread includes a plurality of first monofilament threads and further comprising inserting the plurality of first monofilament threads into the patient's superficial orbital fat pad.

3. The method as recited in claim 1 wherein the at least one second monofilament thread includes a plurality of second monofilament threads and further comprising inserting the plurality of second monofilament threads into the patient's nasolabial fat pad.

4. The method as recited in claim 1 wherein the at least one third monofilament thread includes a plurality of third monofilament threads and further comprising inserting the plurality of third monofilament threads into the patient's jowl fat pad.

5. The method as recited in claim 4 further comprising tying each of the plurality of third monofilament threads in a knot.

6. The method as recited in claim 1 wherein the at least one first monofilament thread comprises a braided configuration.

7. The method as recited in claim 1 wherein the at least one second and third monofilament threads both include at least a portion of anchoring cogs and a portion of lifting cogs.

8. A method for facial, superficial fat pad repositioning in a patient, the method comprising
    identifying at least a first vector to inject at least one monofilament thread, the at least one monofilament thread having a portion of lifting cogs and a portion of anchoring cogs;
    pinching the patient's skin to form a tunnel of subcutaneous fat along the first vector;
    advancing a cannula containing the at least one monofilament thread through the tunnel until resistance from a fat septum is felt;
    upon perforating the fat septum, rotating the cannula, and after rotating the cannula, continuing to advancing the cannula; and
    upon reaching the distal end of the first vector, and before releasing the at least one monofilament thread from the cannula, stretching the skin along the cannula where the anchoring cogs will be deposited and simultaneously lifting the superficial fat pad to the desired location.

9. The method as recited in claim 8 wherein the cannula is rotated approximately 45 degrees.

10. The method as recited in claim 8 wherein the cannula is near the tissue to be lifted and advanced toward an anchor point.

* * * * *

UNITED STATES PATENT AND TRADEMARK OFFICE
CERTIFICATE OF CORRECTION

| | | |
|---|---|---|
| PATENT NO. | : 11,911,255 B1 | Page 1 of 1 |
| APPLICATION NO. | : 17/584040 | |
| DATED | : February 27, 2024 | |
| INVENTOR(S) | : Mariano Busso and Enrique Bonafonte Tortajada | |

It is certified that error appears in the above-identified patent and that said Letters Patent is hereby corrected as shown below:

On the Title Page

Item (12) "Busso" should read -- Busso et al. --.

The inventorship should include Enrique Bonafonte Tortajada, Miami, FL (US) as co-inventor in items (71) Applicant and (72) Inventor.

Signed and Sealed this
Fourteenth Day of October, 2025

John A. Squires
*Director of the United States Patent and Trademark Office*